US008044023B2

(12) United States Patent
Wang et al.

(10) Patent No.: US 8,044,023 B2
(45) Date of Patent: *Oct. 25, 2011

(54) HEPATITIS C VIRUS INHIBITORS

(75) Inventors: Alan Xiangdong Wang, Guilford, CT (US); Paul Michael Scola, Glastonbury, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 148 days.

This patent is subject to a terminal disclaimer.

(21) Appl. No.: 12/473,741

(22) Filed: May 28, 2009

(65) Prior Publication Data

US 2009/0297472 A1 Dec. 3, 2009

Related U.S. Application Data

(60) Provisional application No. 61/056,952, filed on May 29, 2008.

(51) Int. Cl.
*A61K 38/55* (2006.01)
(52) U.S. Cl. .......................................................... 514/4.1
(58) Field of Classification Search .................. None
See application file for complete search history.

(56) References Cited

U.S. PATENT DOCUMENTS

| 5,223,432 | A | 6/1993 | Wirz et al. |
|---|---|---|---|
| 7,449,479 | B2 | 11/2008 | Wang et al. |
| 7,582,605 | B2 | 9/2009 | Moore et al. |
| 7,601,709 | B2 | 10/2009 | Miao et al. |
| 2005/0119168 | A1* | 6/2005 | Venkatraman et al. ......... 514/9 |
| 2005/0153900 | A1* | 7/2005 | Velazquez et al. ............ 514/18 |
| 2005/0164921 | A1* | 7/2005 | Njoroge et al. ................ 514/9 |
| 2005/0209135 | A1 | 9/2005 | Busacca et al. |
| 2006/0199773 | A1 | 9/2006 | Sausker et al. |
| 2006/0257980 | A1 | 11/2006 | Li |
| 2007/0078081 | A1 | 4/2007 | Casarez et al. |
| 2008/0032936 | A1 | 2/2008 | Gai et al. |
| 2008/0039470 | A1 | 2/2008 | Niu et al. |
| 2008/0181868 | A1 | 7/2008 | Sun et al. |
| 2008/0279821 | A1 | 11/2008 | Niu et al. |
| 2009/0202476 | A1 | 8/2009 | Perrone et al. |

FOREIGN PATENT DOCUMENTS

| WO | WO 98/17679 | 4/1998 |
|---|---|---|
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |

(Continued)

OTHER PUBLICATIONS

Tsantrizos et al, "Macrocyclic Inhibitors of the NS3 Protease as Potential Therapeutic Agents of Hepatitis C Virus Infection," Angew. Chem. Int. Ed. (2003), vol. 42, pp. 1356-1360.*
U.S. Appl. No. 12/202,603, filed Sep. 2, 2008, Wang et al.
U.S. Appl. No. 12/418,677, filed Apr. 6, 2009, Sin et al.
U.S. Appl. No. 12/464,954, filed May 13, 2009, Sun et al.
U.S. Appl. No. 12/465,142, filed May 13, 2009, Sin et al.
U.S. Appl. No. 12/473,188, filed May 27, 2009, Wang et al.
Lauer, G.M. et al., "Hepatitis C Virus Infection", The New England Journal of Medicine, vol. 345, No. 1, pp. 41-52 (2001).
Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).

(Continued)

*Primary Examiner* — Cecilia J Tsang
*Assistant Examiner* — Thomas Heard
(74) *Attorney, Agent, or Firm* — Pamela A. Mingo

(57) ABSTRACT

Hepatitis C virus inhibitors having the general formula

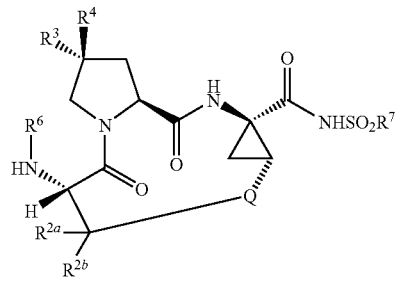

are disclosed. Compositions comprising the compounds and methods for using the compounds to inhibit HCV are also disclosed.

20 Claims, No Drawings

FOREIGN PATENT DOCUMENTS

| | | |
|---|---|---|
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005690 | 1/2009 |
| WO | WO 2009/010804 | 1/2009 |
| WO | WO 2009/014730 | 1/2009 |
| WO | WO 2009/082701 | 7/2009 |
| WO | WO 2009/085659 | 7/2009 |

OTHER PUBLICATIONS

Poupart, M.-A, et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S., "Chemoenzymatic Synthesis of (R)-(—)-Citramalic Acid", Synthesis, pp. 365-366 (1992).

* cited by examiner

HEPATITIS C VIRUS INHIBITORS

CROSS-REFERENCE TO RELATED APPLICATIONS

This application claims the benefit of U.S. Provisional Application Ser. No. 61/056,952 filed May 29, 2008.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS 3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with one or two additional compounds having anti-HCV activity.

In a first aspect the present disclosure provides a compound of formula (I)

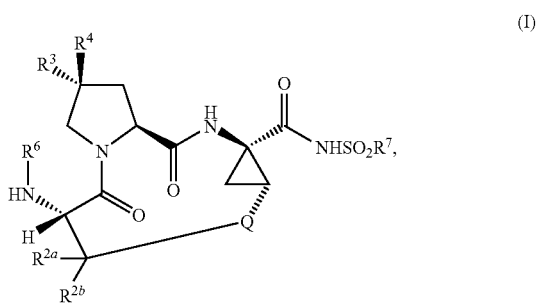

or a pharmaceutically acceptable salt thereof, wherein
  $R^{2a}$ and $R^{2b}$ are independently selected from hydrogen and methyl;
  $R^3$ is selected from alkenyl, alkyl, aryl, arylalkyl, cycloalkyl, (cycloalkyl)aryl, heterocyclyl, and heterocyclylalkyl;
  $R^4$ is selected from —$SR^8$, —$S(O)$—$R^8$, and $SO_2R^8$;
  $R^6$ is selected from hydrogen, alkoxycarbonyl, alkyl, alkylcarbonyl, alkylsulfonyl, cycloalkyloxycarbonyl, cycloalkyl, haloalkoxycarbonyl, haloalkyl, haloalkylcarbonyl, $(NR^eR^f)$carbonyl, and $(NR^eR^f)$sulfonyl; or
  $R^6$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substituents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —$NR^gR^h$, $(NR^jR^k)$carbonyl, $(NR^jR^k)$sulfonyl, and oxo;
  $R^7$ is selected from alkyl, cycloalkyl, and (cycloalkyl)alkyl; wherein the cycloalkyl and the cycloalkyl part of the (cycloalkyl)alkyl are optionally substituted with one group selected from alkenyl, alkoxy, alkyl, and halo;
  $R^8$ is selected from alkoxyalkyl, alkyl, arylalkyl, haloalkoxyalkyl, and haloalkyl; and
  Q is a $C_{5-7}$ saturated or unsaturated chain.

In a first embodiment of the first aspect the present disclosure provides a compound of Formula (I), or a pharmaceutically acceptable salt thereof, wherein $R^7$ is cycloalkyl. In a second embodiment of the first aspect $R^7$ is unsubstituted cycloalkyl.

In a third embodiment of the first aspect the present disclosure provides a compound of Formula (I), or a pharmaceutically acceptable salt thereof, wherein $R^{2a}$ and $R^{2b}$ are each hydrogen.

In a fourth embodiment of the first aspect the present disclosure provides a compound of Formula (I), or a pharmaceutically acceptable salt thereof, wherein $R^3$ is aryl.

In a fifth embodiment of the first aspect the present disclosure provides a compound of Formula (I), or a pharmaceutically acceptable salt thereof, wherein Q is a $C_6$ unsaturated chain.

In a sixth embodiment of the first aspect the present disclosure provides a compound of Formula (I), or a pharmaceutically acceptable salt thereof, wherein $R^8$ is alkyl.

In a second aspect the present disclosure provides a composition comprising a compound of formula (I), or a pharmaceutically acceptable salt thereof, and a pharmaceutically acceptable carrier. In a first embodiment of the second aspect the composition further comprises at least one additional compound having anti-HCV activity. In a second embodiment of the second aspect at least one of the additional compounds is an interferon or a ribavirin. In a third embodiment of the second aspect the interferon is selected from interferon alpha 2B, pegylated interferon alpha, consensus interferon, interferon alpha 2A, and lymphoblastoid interferon tau.

In a fourth embodiment of the second aspect the present disclosure provides a composition comprising a compound of formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the second aspect the present disclosure provides a composition comprising a compound of formula (I), or a pharmaceutically acceptable salt thereof, a pharmaceutically acceptable carrier, and at least one additional compound having anti-HCV activity; wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of formula (I), or a pharmaceutically acceptable salt thereof. In a first embodiment of the third aspect the method further comprises administering at least one additional compound having anti-HCV activity prior to, after, or simultaneously with the compound of formula (I), or a pharmaceutically acceptable salt thereof. In a second embodiment of the third aspect at least one of the additional compounds is an interferon or a ribavirin. In a fourth embodiment of the third aspect the interferon is selected from interferon alpha 2B, pegylated interferon alpha, consensus interferon, interferon alpha 2A, and lymphoblastoid interferon tau.

In a fifth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a sixth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a composition comprising a compound of formula (I), or a pharmaceutically acceptable salt thereof, one, two, three, four, or five additional compounds having anti-HCV activity, and a pharmaceutically acceptable carrier. In a first embodiment of the fourth aspect the composition comprises three or four additional compounds having anti-HCV activity. In a second embodiment of the fourth aspect the composition comprises one or two additional compounds having anti-HCV activity.

In a fifth aspect the present disclosure provides a method of treating an HCV infection in a patient, comprising administering to the patient a therapeutically effective amount of a compound of formula (I), or a pharmaceutically acceptable salt thereof and one, two, three, four, or five additional compounds having anti-HCV activity prior to, after, or simultaneously with the compound of formula (I), or a pharmaceutically acceptable salt thereof. In a first embodiment of the first aspect the method comprises administering three or four additional compounds having anti-HCV activity. In a second embodiment of the first aspect the method comprises administering one or two additional compounds having anti-HCV activity.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term 'aryl'.

In some instances, the number of carbon atoms in any particular group is denoted before the recitation of the group. For example, the term "$C_6$ alkyl" denotes an alkyl group containing six carbon atoms. Where these designations exist they supersede all other definitions contained herein.

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfonyl," as used herein, refers to an alkyl group attached to the patent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure can be optionally substituted with one, two, three, four, or five substituents independently selected from alkoxy, alkoxycarbonyl, alkyl, alkylcarbonyl, a second aryl group, carboxy, cycloalkyl, cycloalkyloxy, cyano, halo, haloalkoxy, haloalkyl, heterocyclyl, nitro, —$NR^cR^d$, ($NR^cR^d$)carbonyl, and oxo; wherein the second aryl group and the heterocyclyl can be further optionally substituted with one, two, three, four, or five substituents independently selected from alkoxy, alkyl, cyano, halo, haloalkoxy, haloalkyl, hydroxy, and nitro.

The term "arylalkyl," as used herein, refers to an alkyl group substituted with one, two, or three aryl groups.

The term "carbonyl," as used herein, refers to —C(O)—.

The term "carboxy," as used herein, refers to —$CO_2H$.

The term "cyano," as used herein, refers to —CN.

The term "cycloalkyl," as used herein, refers to a saturated monocyclic or bicyclic hydrocarbon ring system having three to ten carbon atoms and zero heteroatoms. Representative examples of cycloalkyl groups include, but are not limited to, cyclopropyl, cyclobutyl, and cyclopentyl.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxyalkyl," as used herein, refers to an alkyl group substituted with one, two, or three haloalkoxy groups.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylcarbonyl," as used herein, refers to a haloalkyl group attached to the parent molecular moiety through a carbonyl group.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four- to six-membered aromatic or non-aromatic carbocyclic ring or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocyclyl groups of the present disclosure can be optionally substituted with one, two, three, four, or five substituents independently selected from alkoxy, alkoxycarbonyl, alkyl, alkylcarbonyl, aryl, carboxy, cycloalkyl, cycloalkyloxy, cyano, halo, haloalkoxy, haloalkyl, a second heterocyclyl group, nitro, —$NR^cR^d$, ($NR^cR^d$)carbonyl, and oxo; wherein the aryl and the second heterocyclyl group can be further optionally substituted with one, two, three, four, or five substituents independently selected from alkoxy, alkyl, cyano, halo, haloalkoxy, haloalkyl, hydroxy, and nitro.

The term "heterocyclylalkyl," as used herein, refers to an alkyl group substituted with one, two, or three heterocyclyl groups.

The term "nitro," as used herein, refers to —$NO_2$.

The term "—$NR^cR^d$," as used herein, refers to two groups, $R^c$ and $R^d$, which are attached to the parent molecular moiety through a nitrogen atom. $R^c$ and $R^d$ are independently selected from hydrogen, alkoxycarbonyl, alkyl, and alkylcarbonyl.

The term ($NR^cR^d$)carbonyl," as used herein, refers to an —$NR^cR^d$ group attached to the parent molecular moiety through a carbonyl group.

The term "—$NR^eR^f$," as used herein, refers to two groups, $R^a$ and $R^b$, which are attached to the parent molecular moiety through a nitrogen atom. $R^a$ and $R^b$ are each independently selected from hydrogen, alkoxy, alkoxyalkyl, alkyl, aryl, arylalkyl, cycloalkyl, haloalkoxyalkyl, haloalkyl, heterocyclyl, and heterocyclylalkyl.

The term "(NR$^e$R$^f$)carbonyl," as used herein, refers to an —NR$^e$R$^f$ group attached to the parent molecular moiety through a carbonyl group.

The term "(NR$^e$R$^f$)sulfonyl," as used herein, refers to an —NR$^e$R$^f$ group attached to the parent molecular moiety through a sulfonyl group.

The term "—NR$^g$R$^h$," as used herein, refers to two groups, R$^g$ and R$^h$, which are attached to the parent molecular moiety through a nitrogen atom. R$^g$ and R$^h$ are independently selected from hydrogen, alkoxyalkyl, alkoxycarbonyl, alkyl, alkylcarbonyl, arylalkyl, and haloalkyl.

The term "—NR$^j$R$^k$," as used herein, refers to two groups, R$^j$ and R$^k$, which are attached to the parent molecular moiety through a nitrogen atom. R$^j$ and R$^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

The term "(NR$^j$R$^k$)carbonyl," as used herein, refers to an —NR$^j$R$^k$ group attached to the parent molecular moiety through a carbonyl group.

The term "(NR$^j$R$^k$)sulfonyl," as used herein, refers to an —NR$^j$R$^k$ group attached to the parent molecular moiety through a sulfonyl group.

The term "oxo," as used herein, refers to =O.

The term "sulfonyl," as used herein, refers to —SO$_2$—.

The term "prodrug," as used herein, represents compounds which are rapidly transformed in vivo to the parent compounds by hydrolysis in blood. Prodrugs of the present disclosure include esters of hydroxy groups on the parent molecule, esters of carboxy groups on the parent molecule, and amides of the amines on the parent molecule.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in *Remington's Pharmaceutical Sciences,* 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e., N-terminus first position); whereas P1 starts the numbering from the left hand side of the C-terminus cleavage site, P2: second position from the C-terminus, etc.). (see Berger A. et al., *Transactions of the Royal Society, London series*, B257:249-264 (1970)].

The following figure shows the subsite designations for the compounds of the present disclosure

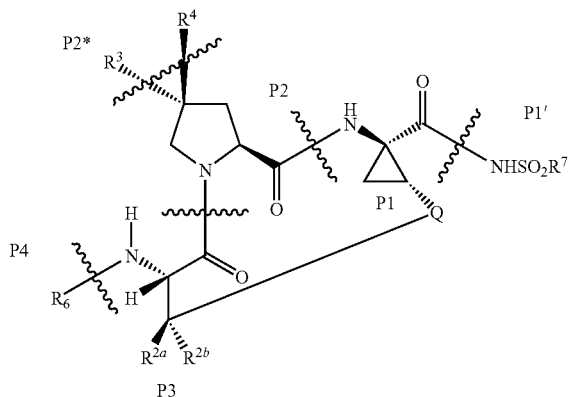

Asymmetric centers exist in the compounds of the present disclosure. For example, the compounds may include P1 cyclopropyl element of formula

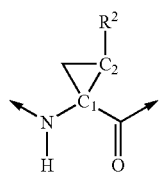

wherein $C_1$ and $C_2$ each represent an asymmetric carbon atom at positions 1 and 2 of the cyclopropyl ring.

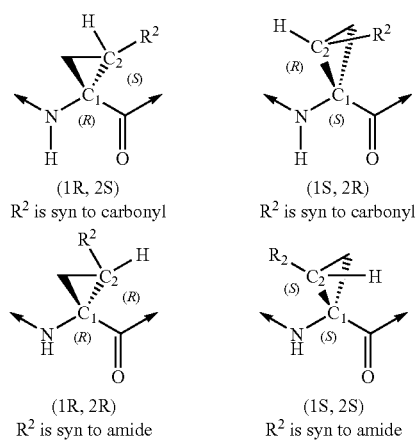

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharm. Res.*, 3(6):318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/ Elan Pharmaceuticals Inc., New York, NY |
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO 2005/047288 26 May 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B replicase inhibitor | Wyeth/ Viropharma |
| NM-283 | Antiviral | NS5B replicase inhibitor | Idenix/Novartis |
| GL-59728 | Antiviral | NS5B replicase inhibitor | Gene Labs/ Novartis |
| GL-60667 | Antiviral | NS5B replicase inhibitor | Gene Labs/ Novartis |
| 2'C MeA | Antiviral | NS5B replicase inhibitor | Gilead |

TABLE 1-continued

| Brand Name | Physiological Class | Type of Inhibitor or Target | Source Company |
|---|---|---|---|
| PSI 6130 | Antiviral | NS5B rephease inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering-Plough |
| Zadazim | Immune modulator | Immune modulator | SciClone Pharmaceuticals Inc., San Mateo, CA |
| Ceplene | Immunomodulator | Immune modulator | Maxim Pharmaceuticals Inc., San Diego, CA |
| CELLCEPT ® | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon - α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | Natural IFN-α | Viragen Inc., Plantation, FL |

TABLE 1-continued

| Brand Name | Physiological Class | Type of Inhibitor or Target | Source Company |
|---|---|---|---|
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering-Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |
| MK-7009 | Antiviral | Serine protease inhibitor | Merck |
| PF-00868554 | Antiviral | Replicase inhibitor | Pfizer |
| ANA598 | Antiviral | Non-nucleoside NS5B polymerase inhibitor | Anadys Pharmaceuticals, Inc., San Diego, CA, USA |
| IDX375 | Antiviral | Non-nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| VCH-759 | Antiviral | NS5B polymerase inhibitor | ViroChem Pharma |
| VCH-916 | Antiviral | NS5B polymerase inhibitor | ViroChem Pharma |
| GS-9190 | Antiviral | NS5B polymerase inhibitor | Gilead |
| Peg-interferon lamda | Antiviral | Interferon | ZymoGenetics/ Bristol-Myers Squibb |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: DMSO for dimethylsulfoxide; THF for tetrahydrofuran; and rt for room temperature or retention time (context will dictate).

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

General Description of Synthesis

The compounds of the present invention may be synthesized as outlined in the generic Scheme 1, and 2.

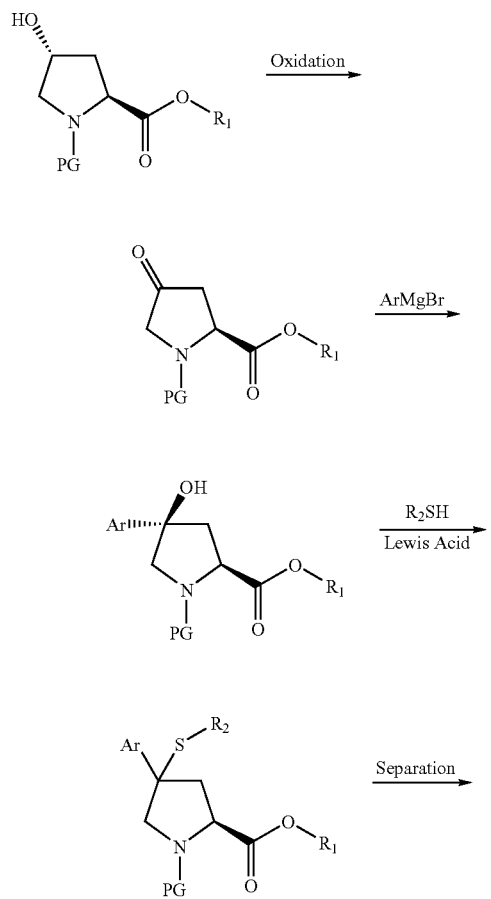

Scheme 1

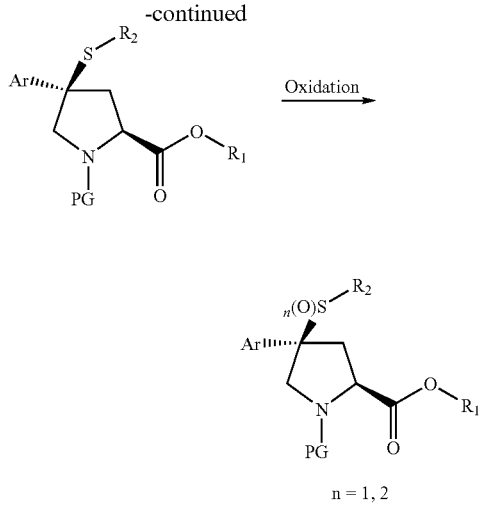

Scheme 2

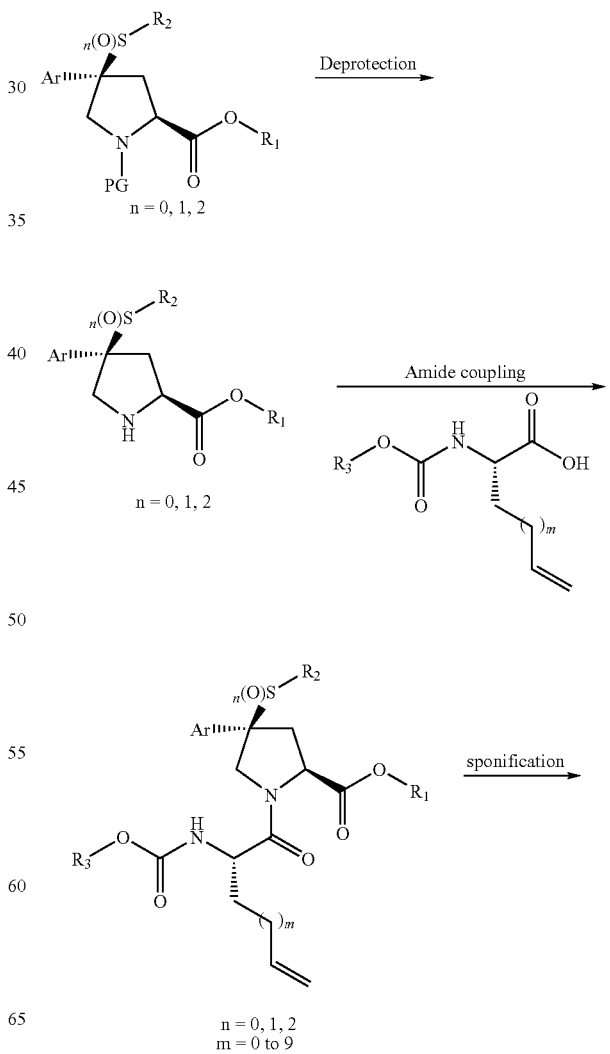

Scheme 2

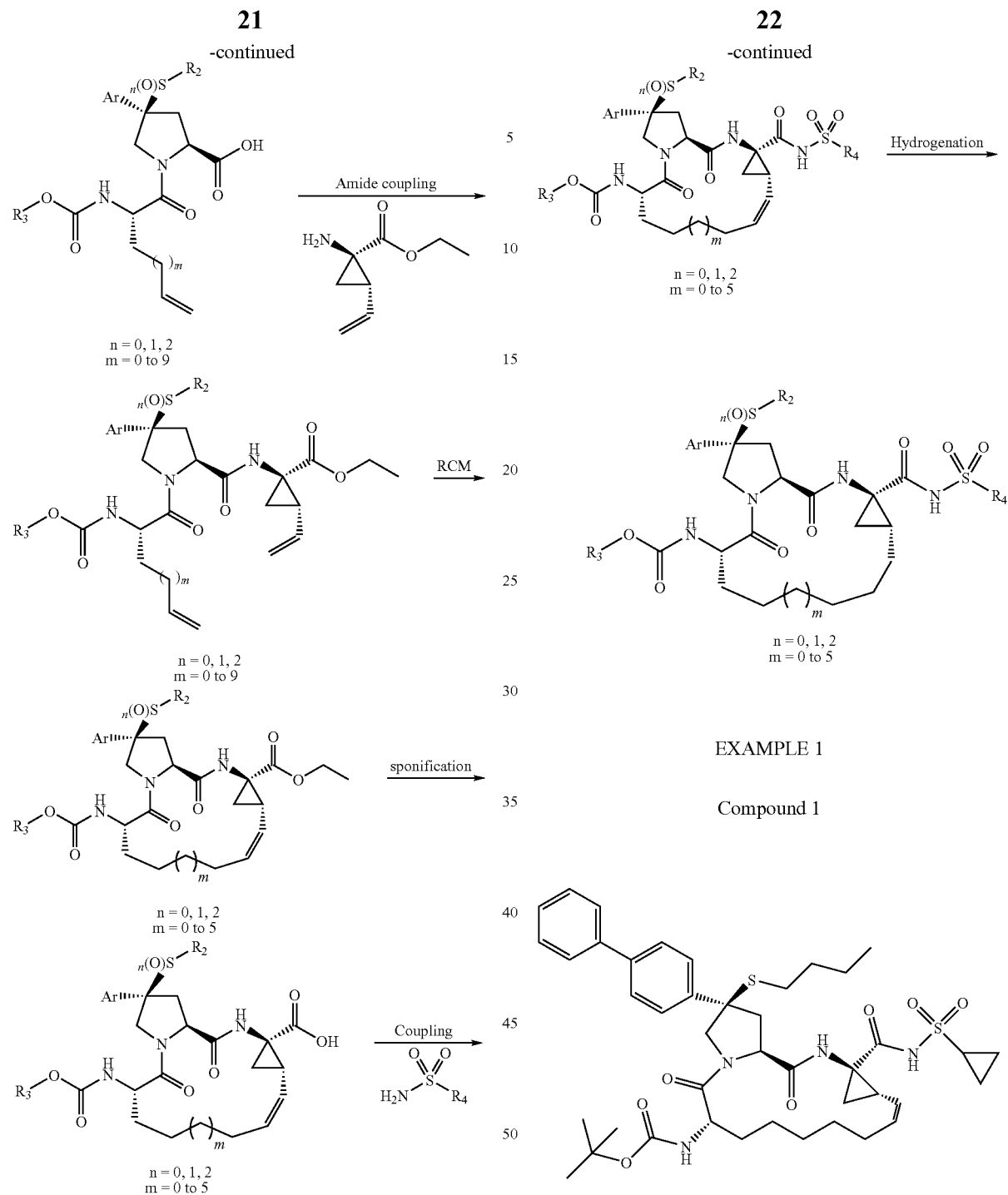
EXAMPLE 1
Compound 1
Scheme 3
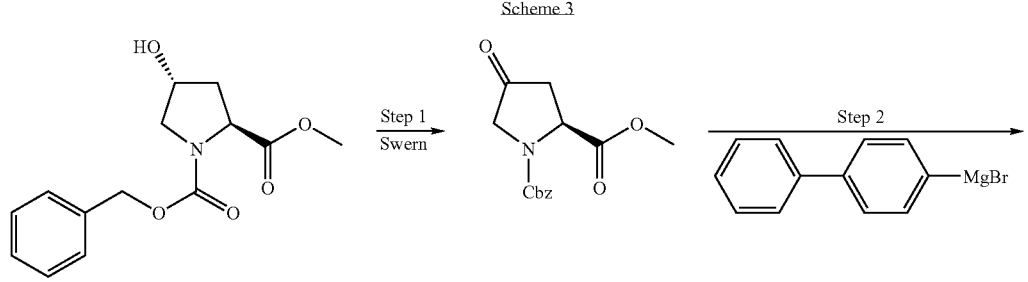

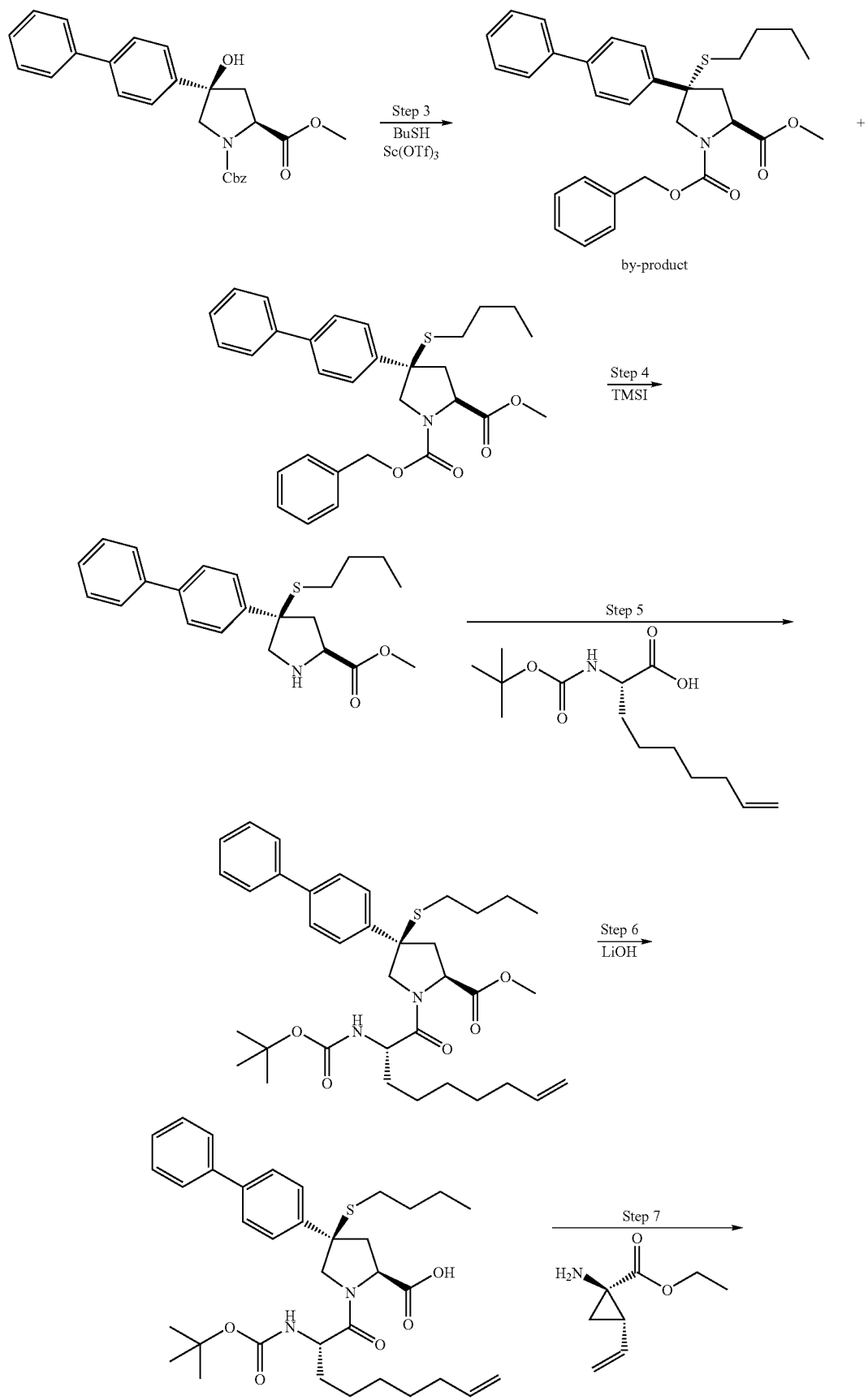

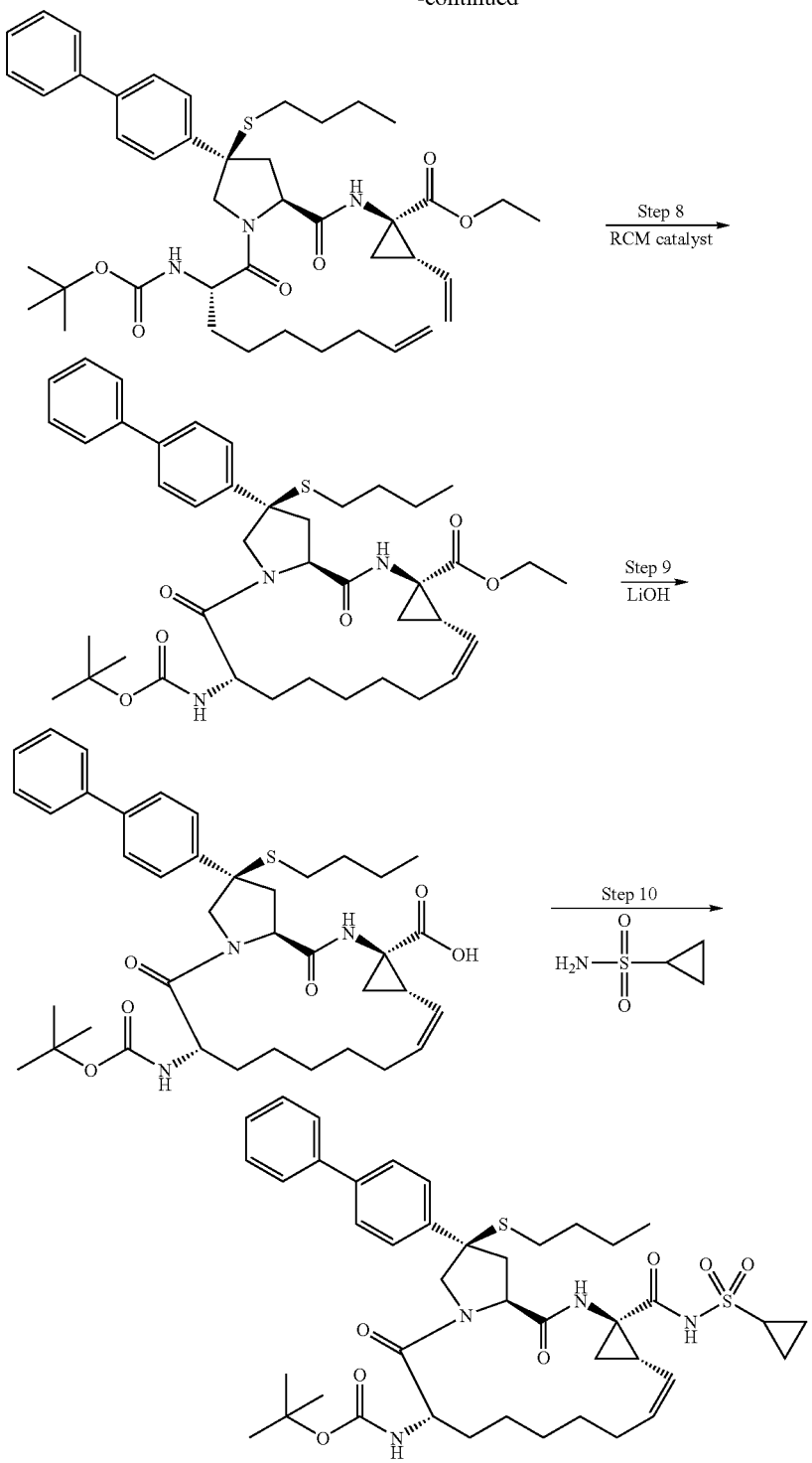

Step 1.

To solution of methyl sulfoxide (28.0 ml, 395 mmol) in dichloromethane (150 ml) at −78 ° C. was added oxalyl chloride (99 ml, 198 mmol) dropwise. The formed solution was stirred at this temperature for 30 minutes. A solution of (2S,4R)-1-benzyl 2-methyl 4-hydroxypyrrolidine-1,2-dicarboxylate (25.08 g, 90 mmol) in dichloromethane (150 ml) was added dropwise at −78° C. The formed white slurry was stirred at −78° C. for 2 hours before addition of N,N-diisopropylethylamine (78 ml, 449 mmol) dropwise. The final pink solution was stirred at room temperature for 3 hours, washed with iced 1M HCl, 5% citric acid, and brine, dried over MgSO$_4$, filtered, and concentrated. The residual light brown oil was purified by column, eluted with 4:1, 3: 1, then 2:1 hexane-ethyl acetate to afford the desired product (17.8 g, 72% yield) as light brown viscous oil. $^1$H NMR (CDCl$_3$) δ

2.58-2.63 (m, 1 H), 2.90-2.99 (m, 1 H), 3.62, 3.77 (s, 3 H, rotamers), 3.95-4.02 (m, 2 H), 4.82-4.89 (m, 1 H), 5.11-5.24 (m, 2 H), 7.32-7.39 (m, 5 H).

Step 2.

To a solution of (S)-1-benzyl 2-methyl 4-oxopyrrolidine-1,2-dicarboxylate (13.24 g, 47.8 mmol) in Toluene (400 mL) at 0° C. was added biphenyl-4-ylmagnesium bromide (124 mL, 62.1 mmol) dropwise. The formed light yellow solution was stirred at this temperature for 1 hour, quenched with $NH_4Cl$, and the organic layer separated. The aqueous phase was extracted with ethyl acetate. Washed the combined organic layers with brine, dried over $MgSO_4$, filtered, and concentrated. The residue was purified by passing through silica gel plug, eluted with 4:1, 3:1 then 2:1, and finally 3:2 hexane-ethyl acetate to provide 10.50 g white solid, which was recrystallized from ethyl acetate-hexane (50 ml-150 ml) to afford 7.50 g of the desired product as a small pink needle. The mother liquor was concentrated and purified by BIOTAGE® column, eluted with 5%~50% EtOAc-hexane to yield additional 1.89 g of the desired product. $^1$H NMR ($CDCl_3$) δ 2.39-2.45 (m, 1 H), 2.70-2.75 (m, 1 H), 3.66, 3.86 (s, 3 H, rotamers), 3.80-3.90 (m, 1 H), 4.00-4.07 (m, 1 H), 4.62 (dd, $J_{1,2}$=9.5, 28 Hz, 1 H), 5.09-5.15 (m, 1 H), 5.21-5.25 (m, 1 H), 7.31-7.38 (m, 6 H), 7.42-7.45 (m, 2 H), 7.54-7.59 (m, 6 H); LC-MS (retention time: 2.77 min, method B), MS m/z 414 ($M^+$-$H_2O$), 370 ($M^+$-$H_2O$—$CO_2$).

Step 3.

To a clear solution of (2S,4R)-1-benzyl 2-methyl 4-(biphenyl-4-yl)-4-hydroxypyrrolidine-1,2-dicarboxylate (2.59 g, 6 mmol) and 1-butanethiol (0.773 mL, 7.20 mmol) in acetonitrile (30 mL) was added Scandium(III) trifluoromethanesulfonate (0.295 g, 0.600 mmol) as solid by one portion at room temperature. The formed pink solution was stirred at this temperature for 26 hours. TLC analysis showed starting material was completely consumed. Quenched with saturated ammonium chloride, extracted with ethyl acetate. Washed the organic phase with brine, dried over $MgSO_4$, filtered, concentrated in vacuo. The residue was purified by BIOTAGE® column, eluted with gradient 5~40% ethyl acetate-hexane to afford the mixture of diastereomers 2.54 g (84%). This oily mixture was purified by BIOTAGE® again, eluted with gradient 0~20% ethyl acetate-toluene. The first peak collected from the column afforded by-product (2S,4S)-1-benzyl 2-methyl 4-(biphenyl-4-yl)-4-(butylthio)pyrrolidine-1,2-dicarboxylate (1.54 g, 2.60 mmol, 43.3% yield) as a wax. $^1$H NMR (500 MHz, CHLOROFORM-d) δ ppm 0.77 (t, J=7.17, 3H), 1.21-1.24 (m, 2 H), 1.28-1.34 (m, 2 H), 2.20-2.29 (m, 2 H), 2.41-2.46 (m, 1 H), 2.86 (dd, J=12.82, 7.32 Hz, 1 H), 3.53, 3.75 (s, rotomer, 3 H), 3.89 (dd, J=17.09, 11.29 Hz, 1 H), 4.23-4.36 (m, 1 H), 4.69-4.77 (m, 1 H) 5.22-5.30 (m, 2 H) 7.28-7.44 (m, 10 H), 7.53-7.60 (m, 4 H). LC-MS (retention time: 3.28 min, method B), MS m/z 504 (M+H).

The desired product (2S,4R)-1-benzyl 2-methyl 4-(biphenyl-4-yl)-4-(butylthio)pyrrolidine-1,2-dicarboxylate (0.96 g, 1.620 mmol, 27.0% yield) was collected as the second peak from the column as a wax. $^1$H NMR (500 MHz, CHLOROFORM-d) δ ppm 0.77 (t, J=7.17, 3 H), 1.18-1.26 (m, 2 H), 1.27-1.35 (m, 2 H), 2.15-2.24 (m, 2 H), 2.64-2.73 (m, 1 H), 2.76-2.84 (m, 1 H), 3.61, 3.77 (s, rotomer, 3 H), 3.93-3.95 (m, 1 H), 4.16-4.30 (m, 1 H), 4.35-4.45 (m, 1 H), 5.03-5.15 (m, 1 H), 5.22 (dd, J=16.02, 12.36 Hz, 1 H), 7.25-7.41 (m, 3 H), 7.33-7.39 (m, 4 H), 7.41-7.46 (m, 3 H), 7.51-7.60 (m, 4 H). LC-MS (retention time: 3.28 min, method B), MS m/z 504 (M+H).

Step 4.

To an iced solution of (2S,4R)-1-benzyl 2-methyl 4-(biphenyl-4-yl)-4-(butylthio)pyrrolidine-1,2-dicarboxylate (1.19 g, 2.363 mmol) in acetonitrile (20 mL) was added iodotrimethylsilane (0.404 mL, 2.84 mmol). The formed light brown solution was stirred at room temperature for 2 hours. Cooled with ice bath, quenched with thiophenol (0.314 mL, 3.07 mmol) and saturated ammonium chloride, extracted with ethyl acetate. The organic layer was washed with brine, dried over $MgSO_4$, filtered. The filtrate was treated with hydrochloric acid (3.54 mL, 7.09 mmol) and concentrated in vacuo. The residual oil was triturated with ether, decanted the ether layer. The remaining gum was pumped to dryness to afford the desired product (2S,4R)-methyl 4-(biphenyl-4-yl)-4-(butylthio)pyrrolidine-2-carboxylate, HCl (952 mg, 1.876 mmol, 79% yield) as a light yellow solid. $^1$H NMR (500 MHz, MeOD) δ ppm 0.78 (t, J=7.22 Hz, 3 H), 1.23-1.32 (m, 4 H), 2.33 (dt, J=11.67, 7.13 Hz, 1 H), 2.37-2.43 (m, 1 H), 2.98 (dd, J=14.19, 10.22 Hz, 1 H), 3.13 (dd, J=14.04, 1.83 Hz, 1 H), 3.81 (d, J=11.90 Hz, 1 H), 3.96 (s, 3 H), 4.02 (d, J=11.90 Hz, 1 H), 4.79 (dd, J=10.38, 2.75 Hz, 1 H), 7.38 (m, 1 H), 7.44-7.52 (m, 4 H), 7.63-7.71 (m, 4 H). LC-MS (retention time: 2.27 min, method B), MS m/z 354 (M+H).

Step 5.

To an iced slurry of (2S,4R)-methyl 4-(biphenyl-4-yl)-4-(butylthio)pyrrolidine-2-carboxylate, HCl (235 mg, 0.579 mmol), (S)-2-(tert-butoxycarbonylamino)non-8-enoic acid (173 mg, 0.637 mmol), and O-(7-azabenzotriazol-1-yl)-N,N,N',N'-tetramethyluronium phosphate HATU, 330 mg, 0.868 mmol) in dichloromethane (6 mL) was added N,N-diisopropylethylamine (0.404 mL, 2.315 mmol). The formed colorless slurry was stirred at room temperature overnight. Diluted with dichloromethane, quenched with 5% citric acid. The organic layer was washed with 0.1 M NaOH and brine, dried over $MgSO_4$, filtered, concentrated in vacuo. The residue was purified by BIOTAGE® column, eluted with 5~35% ethyl acetate-hexane to yield the desired product (2S,4R)-methyl 4-(biphenyl-4-yl)-1-((S)-2-(tert-butoxycarbonylamino)non-8-enoyl)-4-(butylthio)pyrrolidine-2-carboxylate (215 mg, 0.345 mmol, 59.6% yield) as a white foam. $^1$H NMR (500 MHz, MeOD) δ ppm 0.73-0.91 (m, 3 H) 1.14-1.39 (m, 6 H) 1.38-1.60 (m, 14 H) 1.63-1.72 (m, 1 H) 1.75-1.85 (m, 1 H) 2.13 (q, J=6.92 Hz, 2 H) 2.25-2.36 (m, 2 H) 2.64 (dd, J=12.97, 6.26 Hz, 1 H) 2.89 (dd, J=12.97, 8.09 Hz, 1 H) 3.75 (s, 3 H) 4.09 (d, J=10.99 Hz, 1 H) 4.46 (dt, J=10.15, 3.78 Hz, 1 H) 4.68 (d, J=10.68 Hz, 1 H) 4.94-4.98 (m, 1 H) 5.01-5.11 (m, 1 H) 5.79-5.94 (m, J=17.01, 10.15, 6.71, 6.71 Hz, 1 H) 7.36 (t, J=7.48 Hz, 1 H) 7.46 (t, J=7.78 Hz, 2 H) 7.57-7.72 (m, 6 H). LC-MS (retention time: 3.88 min, method C), MS m/z 623 (M+H).

Step 6.

To a solution of (2S,4R)-methyl 4-(biphenyl-4-yl)-1-((S)-2-(tert-butoxycarbonylamino)non-8-enoyl)-4-(butylthio)pyrrolidine-2-carboxylate (135 mg, 0.217 mmol) in THF (1.5 mL) and methanol (1.500 mL) was added pre-made solution of lithium hydroxide monohydrate (18.19 mg, 0.433 mmol) in water (1.5 mL). The resulting cloudy solution was stirred at room for 3 hours. Quenched with 5% citric acid, extracted with ethyl acetate. The organic layer was washed with brine, dried over $MgSO_4$, filtered, concentrated to afford the desired product (2S,4R)-4-(biphenyl-4-yl)-1-((S)-2-(tert-butoxycarbonylamino)non-8-enoyl)-4-(butylthio)pyrrolidine-2-carboxylic acid (129 mg, 0.191 mmol, 88% yield) as a white foam. LC-MS (retention time: 3.67 min, method C), MS m/z 609 (M+H).

Step 7.

To an iced slurry of (2S,4R)-4-(biphenyl-4-yl)-1-((S)-2-(tert-butoxycarbonylamino)-3,3-dimethylnon-8-enoyl)-4-(butylthio)pyrrolidine-2-carboxylic acid (126 mg, 0.198 mmol), (1R,2S)-ethyl 1-amino-2-vinylcyclopropanecarboxylate (36.8 mg, 0.237 mmol), and O-(7-azabenzotriazol-1-yl)-N,N,N',N'-tetramethyluronium phosphate (HATU, 113 mg, 0.297 mmol) in dichloromethane (4 mL) was added N,N-diisopropylethylamine (0. 104 mL, 0.594 mmol). The formed light brown solution was stirred at room temperature overnight. Diluted with ethyl acetate, washed it with 5% citric acid, 0.1 M NaOH, and brine, dried over MgSO$_4$, filtered, and concentrated. The resulting brown residue was purified by BIOTAGE® column, eluted with gradient 5~45% ethyl acetate-hexane to afford the desired product (1R,2S)-ethyl 1-((2S,4R)-4-(biphenyl-4-yl)-1-((S)-2-(tert-butoxycarbonylamino)-3,3-dimethylnon-8-enoyl)-4-(butylthio)pyrrolidine-2-carboxamido)-2-vinylcyclopropanecarboxylate (75 mg, 0.097 mmol, 49.0% yield) as a white film. $^1$H NMR (500 MHz, MeOD) δ ppm 0.75-0.90 (m, 3 H) 1.24-1.54 (m, 24 H) 1.61 (tt, J=9.00, 4.27 Hz, 1 H) 1.65-1.77 (m, 2 H) 1.86 (d, J=7.32 Hz, 1 H) 1.94-2.11 (m, 2 H) 2.19-2.41 (m, 3 H) 2.41-2.51 (m, 1 H) 2.77 (dd, J=13.12, 7.02 Hz, 1 H) 3.03 (dd, J=12.51, 7.63 Hz, 1 H) 3.94-4.04 (m, 1 H) 4.09-4.24 (m, 3 H) 4.35 (t, J=7.48 Hz, 1 H) 5.07-5.18 (m, 1 H) 5.24-5.36 (m, 1 H) 5.70-5.86 (m, 2 H) 7.30-7.41 (m, 1 H) 7.46 (t, J=7.63 Hz, 2 H) 7.58-7.75 (m, 6 H). LC-MS (retention time: 3.72 min, method C), MS m/z 774 (M-C$_2$ H$_4$).

Step 8.

A solution of (1R,2S)-ethyl 1-((2S,4R)-4-(biphenyl-4-yl)-1-((S)-2-(tert-butoxycarbonylamino)-3,3-dimethylnon-8-enoyl)-4-(butylthio)pyrrolidine-2-carboxamido)-2-vinylcyclopropanecarboxylate (75 mg, 0.097 mmol) in dichloromethane (30 mL) was purged with nitrogen for 3 min. And then Hoveyda-Grubbs Catalyst 2nd Generation (73.1 mg, 0.116 mmol) was added. The resulting green solution was heated to reflux for 5 hours. The reaction was quenched with 2-mercaptonicotinic acid (30.1 mg, 0.194 mmol) and washed with saturated Na$_2$CO$_3$, and brine. Dried over MgSO$_4$, filtered, and concentrated in vacuo. The brown residue was purified by BIOTAGE® column, eluted with gradient 5%~50% ethyl acetate-hexane to afford the desired product (2R,6S,13aS,14aR,16aS,Z)-ethyl 2-(biphenyl-4-yl)-6-(tert-butoxycarbonylamino)-2-(butylthio)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (59 mg, 0.074 mmol, 76% yield) as an off-white solid. $^1$H NMR (500 MHz, MeOD) δ ppm 0.83 (t, 3 H) 1.14-1.37 (m, 8 H) 1.38-1.54(m, 17 H) 1.52-1.68 (m, 4 H) 1.79-1.95 (m, 1 H) 1.97-2.10 (m, 1 H) 2.25-2.37 (m, 2 H) 2.37-2.49 (m, 2 H) 2.53 (dd, J=12.51, 10.07 Hz, 1 H) 2.88 (dd, J=12.51, 7.02 Hz, 1 H) 3.97-4.08 (m, 2 H) 4.07-4.22 (m, 3 H) 4.50 (dd, J=10.22, 2.90 Hz, 1 H) 5.17 (d, J=10.68 Hz, 1 H) 5.34 (t, J=9.77 Hz, 1 H) 5.56-5.68 (m, 1 H) 7.30-7.41 (m, 1 H) 7.41-7.50 (m, 2 H) 7.60 (d, J=8.24 Hz, 4 H) 7.77 (d, J=8.24 Hz, 2 H). LC-MS (retention time: 3.55 min, method C), MS m/z 718 (M+H).

Step 9.

To a solution of (2R,6S,13aS,14aR,16aS,Z)-ethyl 2-(biphenyl-4-yl)-6-(tert-butoxycarbonylamino)-2-(butylthio)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (59 mg, 0.082 mmol) in THF (1 mL) and MeOH (1.000 mL) was added pre-made solution of Lithium hydroxide monohydrate (6.90 mg, 0.164 mmol) in water (1 mL). The resulting cloudy solution was stirred at room for 5 h. LC/MS analysis showed partial reaction. Another portion of Lithium hydroxide monohydrate (6.90 mg, 0.164 mmol) in water (0.2 ml) was added and stirred for additional 17 hours. LC/MS analysis showed there was still small portion of starting material remained. Another portion of Lithium hydroxide monohydrate (6.90 mg, 0.164 mmol) in water (0.2 ml) was added and stirred for additional 5 hours. Quenched with 5% citric acid, extracted with ethyl acetate. The organic layer was washed with brine, dried over MgSO$_4$, filtered, and concentrated to afford the desired product (2R,6S,13aS,14aR,16aS,Z)-2-(biphenyl-4-yl)-6-(tert-butoxycarbonylamino)-2-(butylthio)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (57 mg, 0.074 mmol, 90% yield) as a white foam. $^1$H NMR (500 MHz, MeOD) δ ppm 0.84 (t, J=7.32 Hz, 3 H) 1.14-1.37 (m, 5 H) 1.38-1.54 (m, 16 H) 1.53-1.68 (m, 4 H) 1.82-1.95 (m, 1 H) 1.96-2.12 (m, 1 H) 2.21-2.38 (m, 2 H) 2.42 (dt, J=12.21, 7.17 Hz, 1 H) 2.48-2.63 (m, 1 H) 2.84-3.00 (m, 1 H) 3.92-4.18 (m, 2 H) 4.49 (dd, J=10.38, 2.75 Hz, 1 H) 5.18 (d, J=10.68 Hz, 1 H) 5.35 (t, J=9.77 Hz, 1 H) 5.56-5.68 (m, 1 H) 7.30-7.39 (m, 1 H) 7.45 (t, J=7.63 Hz, 2 H) 7.55-7.63 (m, 4 H) 7.77 (d, J=8.24 Hz, 2 H). LC-MS (retention time: 3.34 min, method C), MS m/z 690 (M+H).

Step 10.

A solution of (2R,6S,13aS,14aR,16aS,Z)-2-(biphenyl-4-yl)-6-(tert-butoxycarbonylamino)-2-(butylthio)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (15 mg, 0.022 mmol) and CDI (7.05 mg, 0.043 mmol) in tetrahydrofuran (1 mL) was heated to gentle reflux for 3 h. Cooled down to rt, cyclopropanesulfonamide (5.27 mg, 0.043 mmol) and DBU (9.83 μL, 0.065 mmol) were added and the reaction continued at r.t. overnight. Removed the solvent in vacuo. The residue was purified by prep-HPLC to afford the desired product tert-butyl (2R,6S,13aS,14aR,16aS,Z)-2-(biphenyl-4-yl)-2-(butylthio)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (11 mg, 0.014 mmol, 63.8% yield) as a white solid. $^1$H NMR (500 MHz, MeOD) δ ppm 0.84 (t, J=7.32 Hz, 3 H) 1.00-1.06 (m, 1 H) 1.09-1.17 (m, 2 H) 1.27-1.38 (m,5 H) 1.38-1.47 (m, 5 H) 1.46-1.63 (m, 14 H) 1.70 (dd, J=8.09, 5.34 Hz, 1 H) 1.86-2.00 (m, 2 H) 2.24-2.33 (m, 1 H) 2.39-2.48 (m, 2 H) 2.50-2.58 (m, 1 H) 2.63 (s, 1 H) 2.88-2.97 (m, 2 H) 3.98-4.07 (m,2 H) 4.46 (d, J=9.46 Hz, 1 H) 5.08 (t, J=9.31 Hz, 1 H) 5.28 (d, J=10.38 Hz, 1 H) 5.65-5.75 (m, 1 H) 7.36 (t, J=7.48 Hz, 1 H) 7.46 (t, J=7.63 Hz, 2 H) 7.59 (d, J=8.55 Hz, 4 H) 7.79 (t, J=9.00 Hz, 2 H). LC-MS (retention time: 3.48 min, method C), MS m/z 793(M+H).

LC/MS conditions for Method B:
Start % B=0
Final % B=100
Gradient Time=3 min
Stop Time=4 min
Flow Rate=4 ml/min
Wavelength=220
Solvent A=90% water-10% methanol-0.1% TFA
Solvent B=10% water-90% methanol-0.1% TFA
Column 3=(3) PHENOMENEX®-LUNA 4.6×50mm S10
LC/MS conditions for Method C:
Start % B=30
Final % B100
Gradient Time=3 min
Stop Time=4 min
Flow Rate=4 ml/min
Wavelength=220
Solvent A=90% water-10% methanol-0.1% TFA
Solvent B=10% water-90% methanol-0.1% TFA
Column 3=(3) PHENOMENEX®-LUNA 4.6×50 mm S10

EXAMPLE 2
Compound 2
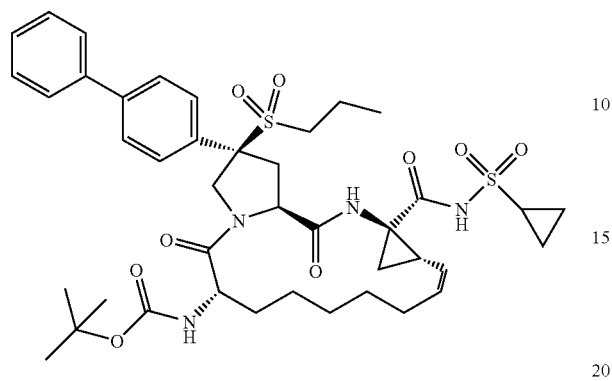
Scheme 4
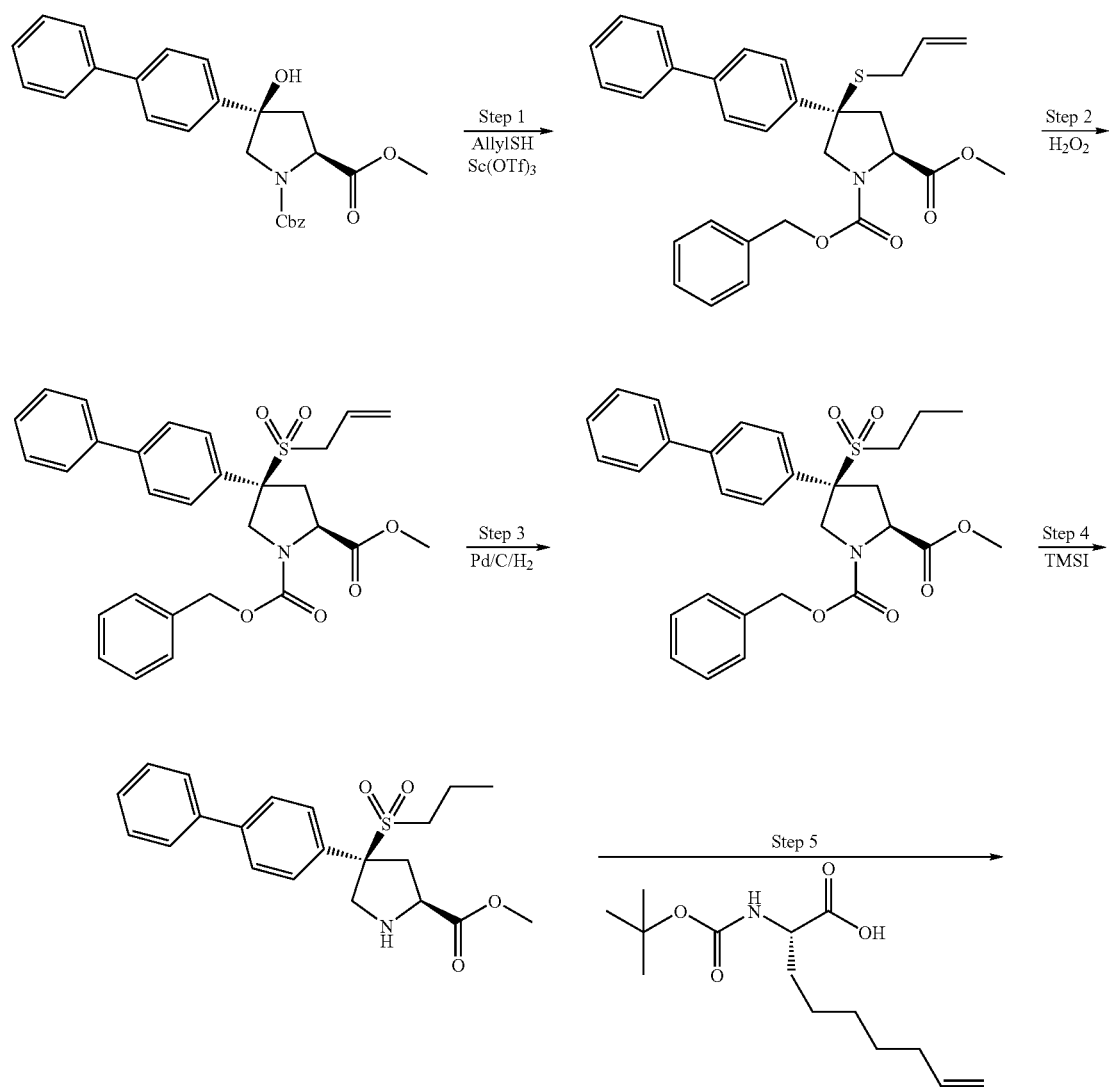

-continued
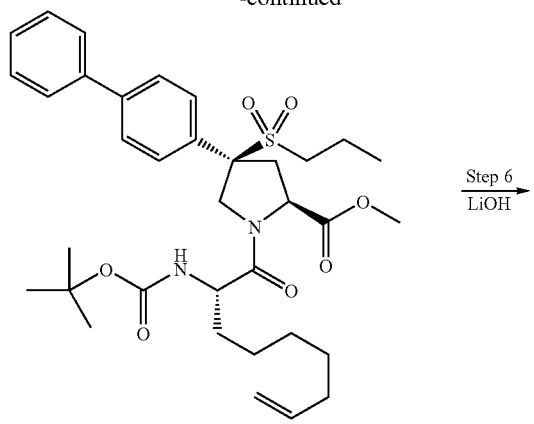
Step 6
LiOH
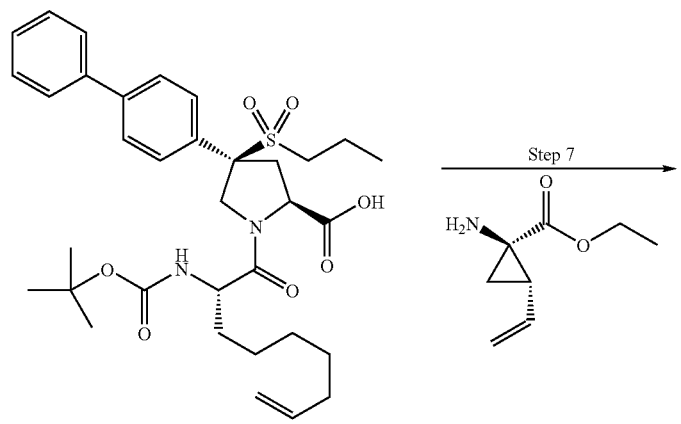
Step 7
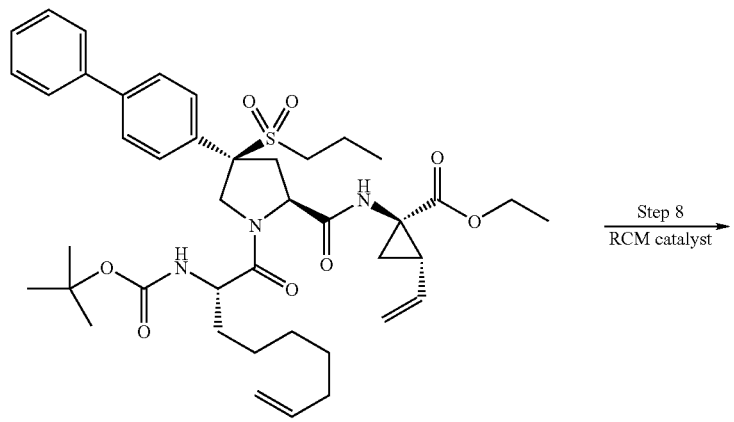
Step 8
RCM catalyst
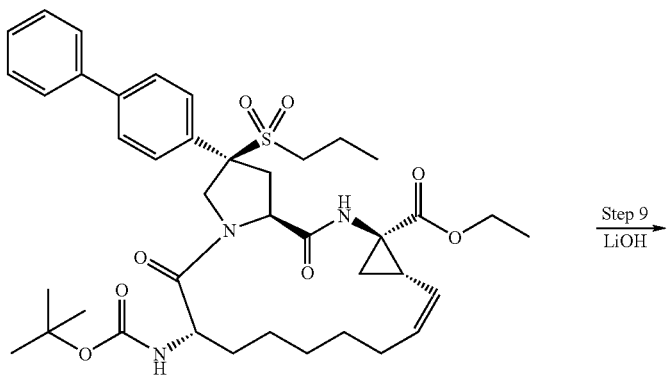
Step 9
LiOH

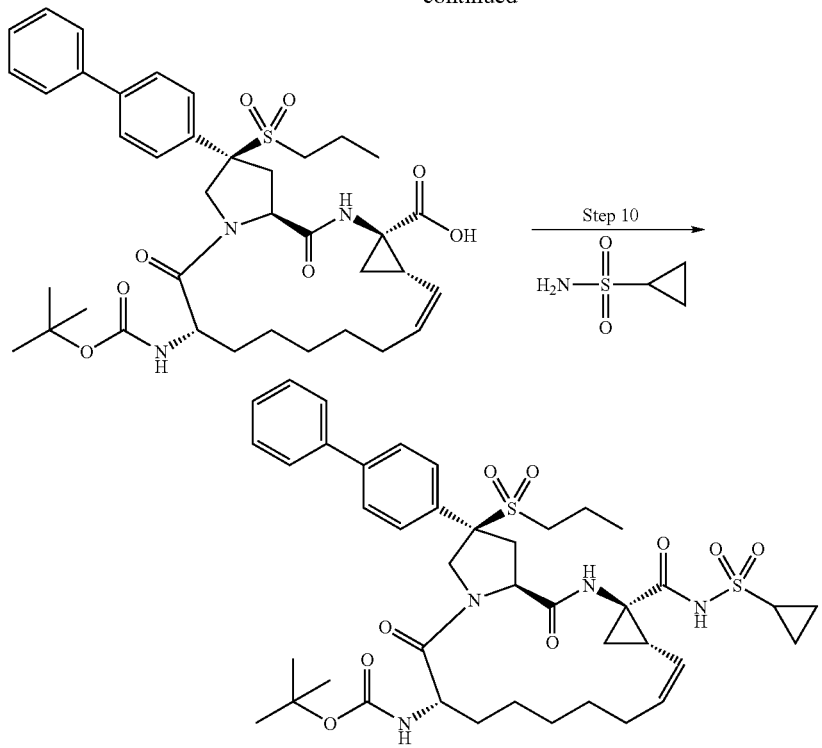

Step 1.

To a clear solution of (2S,4R)-1-benzyl 2-methyl 4-(biphenyl-4-yl)-4-hydroxypyrrolidine-1,2-dicarboxylate (6.48 g, 15.02 mmol) and prop-2-ene-1-thiol (3.18 g, 30.0 mmol) in acetonitrile (70 mL) was added Scandium(III) trifluoromethanesulfonate (0.739 g, 1.502 mmol) as solid by one portion at room temperature. The formed pink solution was stirred at this temperature for 20 h. LC/MS and TLC analysis showed starting material was completely consumed and the desired product was formed. Quenched with sat. ammonium chloride, extracted with EtOAc. Washed the organic with brine, dried over MgSO$_4$, filtered, evaporated in vacuo. The residue was purified by BIOTAGE® column, eluted with 5%~50% EtOAc-Hexane to afford mixture and diastereomers (2.88 g, 79%) and starting material (0.600 g, 18%). This mixture was purified by BIOTAGE® column again, eluted with 2%/~8% EtOAc-toluene to afford the desired product (2S,4R)-1-benzyl 2-methyl 4-(allylthio)-4-(biphenyl-4-yl)pyrrolidine-1,2-dicarboxylate (1.85 g, 3.41 mmol, 22.74% yield) as an viscous oil and the undesired diastereomer plus some overlapped fraction (1.80 g) as an viscous oil. $^1$H NMR (500 MHz, CHLOROFORM-d) δ ppm 2.57-2.74 (m, 1 H) 2.77-2.93 (m, 3 H) 3.56-3.83 (m, 3 H) 3.92 (d, J=11.60 Hz, 1 H) 4.17-4.31 (m, 1 H) 4.33-4.49 (m, 1 H) 4.91-5.08 (m, 2 H) 5.10-5.26 (m, 1 H) 5.63 (ddd, J=17.01, 9.69, 7.17 Hz, 1 H) 7.20-7.41 (m, 7 H) 7.41-7.49 (m, 3 H) 7.49-7.66 (m, 4 H). LC-MS (retention time: 3.32 min, method C), MS m/z 488 (M+H).

Step 2.

Trifluoroacetic acid anhydride (1.451 mL, 10.27 mmol) was added to a stirred slurry of urea hydrogen peroxide (2.58 g, 27.4 mmol) in acetonitrile (50 mL) for 10 min at rt. The formed solution was added through addition funnel to a stirred slurry of (2S,4R)-1-benzyl 2-methyl 4-(allylthio)-4-(biphenyl-4-yl)pyrrolidine-1,2-dicarboxylate (1.67 g, 3.42 mmol) and sodium hydrogen carbonate (1.439 g, 17.12 mmol) in acetonitrile (50 mL) dropwise (it was slightly exothermic). The final mixture was stirred at rt for 1 h. Quenched with water, extracted with EtOAc. The organic layer was washed with brine, dried over MgSO$_4$, filtered, evaporated. The residue was purified by BIOTAGE® system, eluted with gradient 15%~70% EtOAc-hexane to afford the desired product (2S,4R)-1-benzyl 2-methyl 4-(allylsulfonyl)-4-(biphenyl-4-yl)pyrrolidine-1,2-dicarboxylate (1.75 g, 3.37 mmol, 98% yield) as a white solid. $^1$H NMR (400 MHz, MeOD) δ ppm 2.92-3.07 (m, 1 H) 3.29 (d, J=7.78 Hz, 1 H) 3.57 (d, J=6.02 Hz, 2 H) 3.60-3.86 (m, 3 H) 4.17-4.34 (m, 2 H) 4.70 (t, J=9.91 Hz, 1 H) 4.92-5.17 (m, 2 H) 5.17-5.33 (m, 2 H) 5.38 (t, J=8.78 Hz, 1 H) 5.57-5.76 (m, 1 H) 7.17-7.44 (m, 6 H) 7.48 (t, J=7.65 Hz, 2 H) 7.61-7.88 (m, 6 H). LC-MS (retention time: 1.66 min, method A), MS m/z 520 (M+H).

Step 3.

To a vessel containing (2S,4R)-1-benzyl 2-methyl 4-(allylsulfonyl)-4-(biphenyl-4-yl)pyrrolidine-1,2-dicarboxylate (1.90 g, 3.66 mmol) and MeOH (100 mL) was added palladium/C (0.195 g, 0.183 mmol). The vessel was placed on Parr shaker under hydrogen with 25 psi pressure for 4 h. Quenched with CELITE®. Filtered, evaporated to afford the desired product (2S,4R)-1-benzyl 2-methyl 4-(biphenyl-4-yl)-4-(propylsulfonyl)pyrrolidine-1,2-dicarboxylate (1.77 g, 3.39 mmol, 93% yield) as a white solid. $^1$H NMR (400 MHz, MeOD) δ ppm 0.85-1.06 (m, 3 H) 1.64 (dt, J=14.87, 7.50 Hz, 2 H) 2.71-2.82 (m, 1 H) 3.01 (dt, J=13.05, 9.16 Hz, 1 H) 3.25-3.41 (m, 1 H) 3.60-3.84 (m, 3 H) 4.16-4.35 (m, 2 H) 4.69 (dd, J=11.42, 6.65 Hz, 1 H) 4.91-5.28 (m, 2 H) 7.14-7.43 (m, 6 H) 7.44-7.53 (m, 2 H) 7.63-7.88 (m, 6 H). LC-MS (retention time: 1.75 min, method A), MS m/z 522 (M+H).

Step 4.

To a solution of (2S,4R)-1-benzyl 2-methyl 4-(biphenyl-4-yl)-4-(propylsulfonyl)pyrrolidine-1,2-dicarboxylate (1.85 g, 3.55 mmol) in acetonitrile (30 mL) was added iodotrimethylsilane (1.211 mL, 8.51 mmol) at 0° C. The formed light brown solution was stirred at room temperature for 2 h. Cooled with ice bath, quenched with methanol. Removed the volatiles in vacuo. The residual brown oil was triturated with 2M HCl in ether (20 mL). The formed brown solid was filtered. Washed the cake with ether thoroughly. The collected light brown solid was pumped to afford the desired product (2S,4R)-methyl 4-(biphenyl-4-yl)-4-(propylsulfonyl)pyrrolidine-2-carboxylate (1.54 g, 3.19 mmol, 90% yield). $^1$H NMR (500 MHz, MeOD) δ ppm 0.97 (t, J=7.32 Hz, 3 H) 1.57-1.71 (m, 2 H) 2.96 (dd, J=9.16, 5.49 Hz, 1 H) 3.22-3.39 (m, 2 H) 3.65 (dd, J=15.72, 4.73 Hz, 1 H) 3.94 (s, 1 H) 4.14 (d, J=13.12 Hz, 1 H) 4.70 (d, J=13.12 Hz, 1 H) 7.37-7.44 (m, 1 H) 7.45-7.54 (m, 2 H) 7.66 (dd, J=19.99, 7.78 Hz, 4 H) 7.79 (d, J=8.55 Hz, 2 H). LC-MS (retention time: 1.42 min, method A), MS m/z 388 (M+H).

Step 5.

To a slurry of (2S,4R)-methyl 4-(biphenyl-4-yl)-4-(propylsulfonyl)pyrrolidine-2-carboxylate, HCl (1.505 g, 3.55 mmol), (S)-2-(tert-butoxycarbonylamino)non-8-enoic acid (1.060 g, 3.90 mmol), and HATU (2.022 g, 5.32 mmol) in DCM (35 mL) was added N,N-diisopropylethylamine (3.10 mL, 17.75 mmol) dropwise with an ice bath. The formed colorless slurry was stirred at room temperature overnight. Diluted with DCM, washed with 5% citric acid. The organic layer was washed with 0.1 M NaOH and brine, dried over MgSO$_4$, filtered, evaporated in vacuo. The residue was purified by BIOTAGE® column, eluted with 10~60% EtOAc-hexane to yield the desired product (2S,4R)-methyl 4-(biphenyl-4-yl)-1-((S)-2-(tert-butoxycarbonylamino)non-8-enoyl)-4-(propylsulfonyl)pyrrolidine-2-carboxylate (1.52 g, 2.135 mmol, 60.1% yield) as a white foam. $^1$H NMR (400 MHz, MeOD) δ ppm 0.87-1.03 (m, 3 H) 1.35-1.57 (m, 13 H) 1.57-1.72 (m, 3 H) 1.72-1.84 (m, 1 H) 2.11 (q, J=6.61 Hz, 2 H) 2.74-2.86 (m, 2 H) 2.94 (dd, J=13.30, 9.79 Hz, 1 H) 3.27 (dd, J=13.05, 7.28 Hz, 1 H) 3.71, 3.91 (s, 3 H) 4.28 (dd, J=9.41, 7.65 Hz, 1 H) 4.41 (d, J=11.04 Hz, 1 H) 4.47-4.56 (m, 1 H) 4.92-4.99 (m, 1 H) 5.03 (dd, J=17.19, 1.63 Hz, 1 H) 5.12 (d, J=11.29 Hz, 1 H) 5.78-5.92 (m, 1H) 7.34-7.43 (m, 1 H) 7.43-7.54 (m, 2 H) 7.62-7.72 (m, 2 H) 7.71-7.82 (m, 2 H) 7.91 (d, J=8.53 Hz, 2 H). LC-MS (retention time: 2.06 min, method A), MS m/z 641 (M+H).

Step 6.

To a solution of (2S,4R)-methyl 4-(biphenyl-4-yl)-1-((S)-2-(tert-butoxycarbonylamino)non-8-enoyl)-4-(propylsulfonyl)pyrrolidine-2-carboxylate (1.52 g, 2.372 mmol) in THF (20.00 mL) and MeOH (20 mL) was added pre-made solution of lithium hydroxide (0.199 g, 4.74 mmol) in water (20.00 mL). The formed cloudy solution was stirred at rt for 3 h. Removed the volatiles in vacuo. The residue was acidified with 1M HCl to pH 3, extracted with EtOAc. The organic layer was washed with brine, dried over MgSO$_4$, filtered, evaporated in vacuo to afford the desired product (2S,4R)-4-(biphenyl-4-yl)-1-((S)-2-(tert-butoxycarbonylamino)non-8-enoyl)-4-(propylsulfonyl)pyrrolidine-2-carboxylic acid (1.45 g, 2.198 mmol, 93% yield) as a white foam. $^1$H NMR (400 MHz, MeOD) δ ppm 0.97 (t, J=7.53 Hz, 3 H) 1.36-1.55 (m, 12 H) 1.55-1.82 (m, 4 H) 2.10 (q, J=6.61 Hz, 2 H) 2.81 (dd, J=8.66, 6.65 Hz, 2 H) 2.91 (dd, J=12.92, 10.42 Hz, 1 H) 3.28 (d, J=7.28 Hz, 1 H) 4.20 (dd, J=9.91, 7.40 Hz, 1 H) 4.37 (d, J=11.04 Hz, 1 H) 4.52 (t, J=6.90 Hz, 1 H) 4.95 (dd, J=10.16, 1.13 Hz, 2 H) 4.98-5.07 (m, 1 H) 5.13 (d, J=11.04 Hz, 1 H) 5.77-5.94 (m, 1 H) 7.33-7.42 (m, 1 H) 7.48 (t, J=7.53 Hz, 2 H) 7.65 (d, J=7.53 Hz, 2 H) 7.72-7.78 (m, 2 H) 7.93 (d, J=8.28 Hz, 2 H). LC-MS (retention time: 1.99 min, method A), MS m/z 627 (M+H).

Step 7.

To slurry of (2S,4R)-4-(biphenyl-4-yl)-1-((S)-2-(tert-butoxycarbonylamino)non-8-enoyl)-4-(propylsulfonyl)pyrrolidine-2-carboxylic acid (1.45 g, 2.313 mmol), (1R,2S)-ethyl 1-amino-2-vinylcyclopropanecarboxylate, HCl (0.532 g, 2.78 mmol), and HATU (1.319 g, 3.47 mmol) in DCM (30 mL) was added N,N-diisopropylethylamine (1.212 mL, 6.94 mmol) dropwise with ice bath. The formed light brown solution was stirred at room temperature overnight. Washed it with 5% citric acid, 0.1 M NaOH, and brine, dried over MgSO$_4$, filtered, evaporated. The resulting brown residue was purified by BIOTAGE® column, eluted with gradient 15%~70% EtOAc-hexane to afford the desired product (1R,2S)-ethyl 1-((2S,4R)-4-(biphenyl-4-yl)-1-((S)-2-(tert-butoxycarbonylamino)non-8-enoyl)-4-(propylsulfonyl)pyrrolidine-2-carboxamido)-2-vinylcyclopropanecarboxylate (1.47 g, 1.828 mmol, 79% yield) as a white foam. $^1$H NMR (500 MHz, MeOD) δ ppm 0.97 (t, J=7.32 Hz, 6 H) 1.24-1.41 (m, 6 H) 1.38-1.46 (m, 3 H) 1.51 (s, 6 H) 1.56-1.81 (m, 6 H) 2.00 (t, J=6.56 Hz, 1 H) 2.28-2.50 (m, 1 H) 2.70-2.87 (m, 2 H) 2.93 (dd, J=13.12, 10.99 Hz, 1 H) 4.09-4.25 (m, 3 H) 4.31 (t, J=7.32 Hz, 1 H) 4.38 (d, J=10.99 Hz, 1 H) 4.70-4.85 (m, 1 H) 4.93-5.05 (m, 2 H) 5.06-5.18 (m, 2 H) 5.25-5.41 (m, 2 H) 5.69-5.87 (m, 2 H) 7.36-7.45 (m, 1 H) 7.49 (t, J=7.63 Hz, 2 H) 7.61-7.71 (m, 2 H) 7.73-7.81 (m, 2 H) 7.81-7.99 (m, 2 H). LC-MS (retention time: 2.07 min, method A), MS m/z 764 (M+H).

Step 8.

A solution of (1R,2S)-ethyl 1-((2S,4R)-4-(biphenyl-4-yl)-1-((S)-2-(tert-butoxycarbonylamino)non-8-enoyl)-4-(propylsulfonyl)pyrrolidine-2-carboxamido)-2-vinylcyclopropanecarboxylate (1.36 g, 1.78 mmol) in dichloromethane (400 mL) was purged with nitrogen for 2 min. And then Hoveyda-Grubbs Catalyst 2nd Generation (6.25 mg, 9.95 μmol) was added. The resulted pink solution was heated to reflux for 4 h. Removed the solvent in vacuo. The brown residue was purified by BIOTAGE® column, eluted with gradient 15%~70% EtOAc-hexane to afford the desired product (2R,6S,13aS,14aR,16aS,Z)-ethyl 2-(biphenyl-4-yl)-6-(tert-butoxycarbonylamino)-5,16-dioxo-2-(propylsulfonyl)-1,2,3,5,6,7,8,9,10,11,13a,14,14a,15,16,16a-hexadecahydrocyclopropa[e]pyrrolo[1,2-a][1,4]diazacyclopentadecine-14a-carboxylate (1.12 g, 1.52 mmol, 85.0% yield) as an off-white solid. $^1$H NMR (400 MHz, MeOD) δ ppm 0.98 (t, J=7.40 Hz, 3 H) 1.20-1.33 (m, 4 H) 1.37-1.53 (m, 12 H) 1.53-1.66 (m, 3 H) 1.64-1.79 (m, 2 H) 1.79-1.91 (m, 1 H) 1.94-2.08 (m, 1 H) 2.31 (q, J=8.95 Hz, 1 H) 2.40-2.55 (m, 1 H) 2.75-2.90 (m, 2 H) 3.04-3.13 (m, 1 H) 3.13-3.25 (m, 1 H) 4.00-4.23 (m, 3 H) 4.40 (d, J=10.79 Hz, 1 H) 4.47 (dd, J=10.29, 2.76 Hz, 1 H) 5.25-5.42 (m, 2 H) 5.55-5.67 (m, 1 H) 7.34-7.43 (m, 1 H) 7.48 (t, J=7.53 Hz, 2 H) 7.63 (d, J=7.28 Hz, 2 H) 7.72 (d, J=8.53 Hz, 2 H) 7.99 (d, J=8.53 Hz, 2 H). LC-MS (retention time: 1.93 min, method A), MS m/z 736 (M+H).

Step 9.

To a solution of (2R,6S,13aS,14aR,16aS,Z)-ethyl 2-(biphenyl-4-yl)-6-(tert-butoxycarbonylamino)-5,16-dioxo-2-(propylsulfonyl)-1,2,3,5,6,7,8,9,10,11,13a,14,14a,15,16,16a-hexadecahydrocyclopropa[e]pyrrolo[1,2-a][1,4]diazacyclopentadecine-14a-carboxylate (996 mg, 1.353 mmol) in THF (10 mL) and MeOH (10.00 mL) was added pre-made solution of lithium hydroxide monohydrate (341 mg, 8.12 mmol) in water (10 mL). The resulting cloudy solution was heated to gentle reflux for 3 h. Cooled to rt, quenched with 5% citric acid, extracted with EtOAc. The organic layer was washed with brine, dried over MgSO$_4$, filtered, evaporated, to afford the desired product (2R,6S, 13aS,14aR,16aS,Z)-2-(biphenyl-4-yl)-6-(tert-butoxycarbonylamino)-5,16-dioxo-2-(propylsulfonyl)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (949 mg, 1.274 mmol, 94% yield) as a white foam. $^1$H NMR (400 MHz, MeOD) δ ppm 0.98 (t, J=7.40 Hz, 3 H) 1.21-1.33 (m, 1 H) 1.34-1.54 (m, 16 H) 1.51-1.64 (m, 5 H) 1.64-1.78 (m, 2 H) 1.80-1.92 (m, 1 H) 1.92-2.09 (m, 1 H) 2.32 (q, J=8.95 Hz, 1 H) 2.52 (br. s., 1 H) 2.72-2.90 (m, 2 H) 3.03-3.12 (m, 1 H) 3.13-3.23 (m, 1 H) 4.03-4.19 (m, 1 H) 4.39 (d, J=10.54 Hz, 1 H) 4.45 (dd, J=10.29, 2.76 Hz, 1 H) 5.25-5.42 (m, 2 H) 5.54-5.68 (m, 1 H) 7.32-7.43 (m, 1 H) 7.47 (t, J=7.53 Hz, 2 H) 7.63 (d, J=7.28 Hz, 2 H) 7.71 (d, J=8.53 Hz, 2 H) 7.98 (d, J=8.28 Hz, 2 H). LC-MS (retention time: 1.84 min, method A), MS m/z 708 (M+H).

Step 10.

A solution of (2R,6S,13aS,14aR,16aS,Z)-2-(biphenyl-4-yl)-6-(tert-butoxycarbonylamino)-5,16-dioxo-2-(propylsulfonyl)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (995 mg, 1.406 mmol) and CDI (274 mg, 1.687 mmol) in tetrahydrofuran (20 mL) was heated to gentle reflux for 3 h. Cooled down to rt, cyclopropanesulfonamide (204 mg, 1.687 mmol) and DBU (0.424 mL, 2.81 mmol) were added and the reaction continued at r.t. for 4 h. Removed the solvent in vacuo. The residue was taken up in EtOAc. Washed it with 5% citric acid and brine, dried over MgSO$_4$, filtered, evaporated. The residue was purified by BIOTAGE® system, eluted with gradient 10%~50% acetone-hexane to afford the desired product tert-butyl (2R,6S,13aS,14aR,16aS,Z)-2-(biphenyl-4-yl)-14a-(cyclopropylsulfonylcarbamoyl)-5,16-dioxo-2-(propylsulfonyl)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (827 mg, 0.999 mmol, 71.1% yield) as a white solid. $^1$H NMR (400 MHz, MeOD) δ ppm 0.87-1.09 (m, 5 H) 1.06-1.22 (m, 2 H) 1.24-1.40 (m, 3 H) 1.39-1.66 (m, 17 H) 1.64-1.79 (m, 3 H) 1.82-2.03 (m, 2 H) 2.39 (d, J=8.53 Hz, 1 H) 2.65 (br. s., 1 H) 2.75-3.01 (m, 3 H) 3.05-3.27 (m, 2 H) 4.14 (dd, J=10.04, 6.53 Hz, 1 H) 4.43 (d, J=10.54 Hz, 2 H) 4.54 (s, 1 H) 5.11 (br. s., 1 H) 5.34 (d, J=10.54 Hz, 1 H) 5.70 (q, J=8.53 Hz, 1 H) 7.35-7.43 (m, 1 H) 7.48 (t, J=7.65 Hz, 2 H) 7.63 (d, J=7.53 Hz, 2 H) 7.72 (d, J=8.28 Hz, 2 H) 7.98 (d, J=8.28 Hz, 2 H). LC-MS (retention time: 1.92 min, method A), MS m/z 811 (M+H).

LC/MS conditions for Method A:
Start % B=30
Final % B=100
Gradient Time=2 min
Stop Time=3 min
Flow Rate=4 ml/min
Wavelength=220
Solvent A=90% water-10% methanol-0.1% TFA
Solvent B=10% water-90% methanol-0.1% TFA
Column 3=(3) PHENOMENEX®-LUNA 4.6×50 mm S10

LC/MS conditions for Method B:
Start % B=30
Final % B=100
Gradient Time=3 min
Stop Time=4 min
Flow Rate=4 ml/min
Wavelength=220
Solvent A=90% water-10% methanol-0.1% TFA
Solvent B=10% water-90% methanol-0.1% TFA
Column 3=(3) PHENOMENEX®-LUNA 4.6×50 mm S10

LC/MS conditions for Method C:
Start % B=0
Final % B=100
Gradient Time=3 min
Stop Time=4 min
Flow Rate=4 ml/min
Wavelength=220
Solvent A=90% water-10% methanol-0.1% TFA
Solvent B=10% water-90% methanol-0.1% TFA
Column 3=(3) PHENOMENEX®-LUNA 4.6×50 mm S10

Biological Studies

HCV NS3/4A protease complex enzyme assays and cell-based HCV replicon assays can be utilized in the present disclosure, and can be prepared, conducted and validated as described in the art (see, for Example, WO 2008/064061).

Compound 1 was tested as described above and found to have an IC$_{50}$ (NS3/4A BMS Strain) of 4 nM. The EC$_{50}$ is 5 nM.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

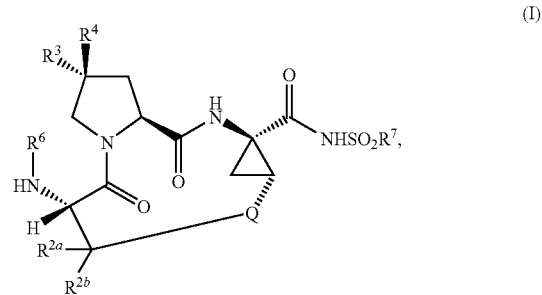

or a pharmaceutically acceptable salt thereof, wherein
R$^{2a}$ and R$^{2b}$ are independently selected from hydrogen and methyl;
R$^3$ is selected from alkenyl, alkyl, aryl, arylalkyl, cycloalkyl, (cycloalkyl)alkyl, heterocyclyl, and heterocyclylalkyl;
R$^4$ is selected from —SR$^8$, —S(O)—R$^8$, and SO$_2$R$^8$;
R$^6$ is selected from hydrogen, alkoxycarbonyl, alkyl, alkylcarbonyl, alkylsulfonyl, cycloalkyloxycarbonyl, cycloalkyl, haloalkoxycarbonyl, haloalkyl, haloalkylcarbonyl, (NR$^e$R$^f$)carbonyl, and (NR$^e$R$^f$)sulfonyl; or
R$^6$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substituents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —NR$^g$R$^h$, (NR$^j$R$^k$)carbonyl, (NR$^j$R$^k$)sulfonyl, and oxo;
R$^7$ is selected from alkyl, cycloalkyl, and (cycloalkyl)alkyl; wherein the cycloalkyl and the cycloalkyl part of the (cycloalkyl)alkyl are optionally substituted with one group selected from alkenyl, alkoxy, alkyl, and halo;

$R^8$ is selected from alkoxyalkyl, alkyl, arylalkyl, haloalkoxyalkyl, and haloalkyl; and Q is a $C_{5-7}$ saturated or unsaturated chain.

2. A compound of claim 1, or a pharmaceutically acceptable salt thereof, wherein $R^7$ is cycloalkyl.

3. A compound of claim 2, or a pharmaceutically acceptable salt thereof, wherein $R^7$ is unsubstituted cycloalkyl.

4. A compound of claim 1, or a pharmaceutically acceptable salt thereof, wherein $R^{2a}$ and $R^{2b}$ are each hydrogen.

5. A compound of claim 1, or a pharmaceutically acceptable salt thereof, wherein $R^3$ is aryl.

6. A compound of claim 1, or a pharmaceutically acceptable salt thereof, wherein Q is a $C_6$ unsaturated chain.

7. A compound of claim 1, or a pharmaceutically acceptable salt thereof, wherein $R^8$ is alkyl.

8. A compound which is

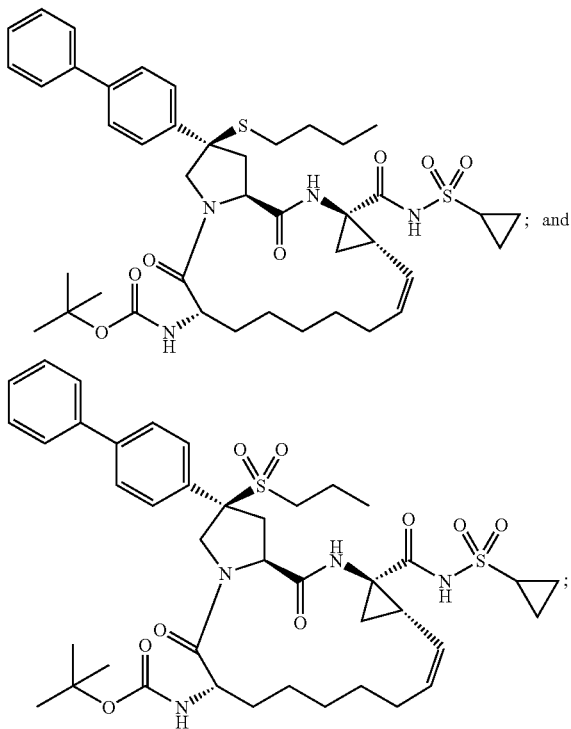

or a pharmaceutically acceptable salt thereof.

9. A composition comprising the compound of claim 1, or a pharmaceutically acceptable salt thereof, and a pharmaceutically acceptable carrier.

10. The composition of claim 9 further comprising at least one additional compound having anti-HCV activity.

11. The composition of claim 10 wherein at least one of the additional compounds is an interferon or a ribavirin.

12. The composition of claim 11 wherein the interferon is selected from interferon alpha 2B, pegylated interferon alpha, consensus interferon, interferon alpha 2A, and lymphoblastoid interferon tau.

13. The composition of claim 10 wherein at least one of the additional compounds is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

14. The composition of claim 10 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

15. A method of treating an HCV infection in a patient, comprising administering to the patient a therapeutically effective amount of a compound of claim 1, or a pharmaceutically acceptable salt thereof.

16. The method of claim 15 further comprising administering at least one additional compounds having anti-HCV activity prior to, after, or simultaneously with the compound of claim 1, or a pharmaceutically acceptable salt thereof.

17. The method of claim 16 wherein at least one of the additional compounds is an interferon or a ribavirin.

18. The method of claim 17 wherein the interferon is selected from interferon alpha 2B, pegylated interferon alpha, consensus interferon, interferon alpha 2A, and lymphoblastoid interferon tau.

19. The method of claim 16 wherein at least one of the additional compounds is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

20. The method of claim 16 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO. : 8,044,023 B2
APPLICATION NO. : 12/473741
DATED : October 25, 2011
INVENTOR(S) : Alan Xiangdong Wang et al.

It is certified that error appears in the above-identified patent and that said Letters Patent is hereby corrected as shown below:

Column 3, line 28, change "Imiqimod" to -- Imiquimod --.

Column 3, line 29, change "5'-monophospate" to -- 5'-monophosphate --.

Column 4, line 1, change "Imiqimod" to -- Imiquimod --.

Column 4, line 2, change "5'-monophospate" to -- 5'-monophosphate --.

Claim 13:

Column 42, line 15, change "Imiqimod" to -- Imiquimod --.

Column 42, line 16, change "5'-monophospate" to -- 5'-monophosphate --.

Claim 19:

Column 42, line 41, change "Imiqimod" to -- Imiquimod --.

Column 42, line 42, change "5'-monophospate" to -- 5'-monophosphate --.

Signed and Sealed this
Fourth Day of September, 2012

David J. Kappos
*Director of the United States Patent and Trademark Office*